United States Patent
Struck

(10) Patent No.: US 10,954,298 B2
(45) Date of Patent: Mar. 23, 2021

(54) METHOD OF OBTAINING A BINDER TO PREPRO-VASOPRESSIN OR FRAGMENTS THEREOF

(71) Applicant: B.R.A.H.M.S. GmbH, Hennigsdorf (DE)

(72) Inventor: Joachim Struck, Berlin (DE)

(73) Assignee: B.R.A.H.M.S. GmbH, Hennigsdorf (DE)

( * ) Notice: Subject to any disclaimer, the term of this patent is extended or adjusted under 35 U.S.C. 154(b) by 181 days.

(21) Appl. No.: 15/967,868

(22) Filed: May 1, 2018

(65) Prior Publication Data

US 2018/0252732 A1    Sep. 6, 2018

Related U.S. Application Data

(62) Division of application No. 14/127,656, filed as application No. PCT/EP2012/002697 on Jun. 26, 2012, now abandoned.

(30) Foreign Application Priority Data

Jun. 30, 2011 (EP) .................................. 11005371

(51) Int. Cl.
| | | |
|---|---|---|
| C07K 16/26 | (2006.01) | |
| G01N 33/68 | (2006.01) | |
| G01N 33/74 | (2006.01) | |
| C07K 7/16 | (2006.01) | |

(52) U.S. Cl.
CPC .............. *C07K 16/26* (2013.01); *C07K 7/16* (2013.01); *G01N 33/6878* (2013.01); *G01N 33/74* (2013.01); *C07K 2317/34* (2013.01); *G01N 2410/04* (2013.01)

(58) Field of Classification Search
CPC ...... G01N 33/74; G01N 2410/04; C07K 7/16; C07K 16/26; C07K 2317/34
See application file for complete search history.

(56) References Cited

U.S. PATENT DOCUMENTS

| 5,686,255 A | 11/1997 | Deth |
|---|---|---|
| 2009/0221009 A1 | 9/2009 | Bergmann et al. |

FOREIGN PATENT DOCUMENTS

| EP | 1488209 A1 | 12/2004 |
|---|---|---|
| EP | 1539818 A2 | 6/2005 |
| EP | 1738178 A1 | 1/2007 |
| WO | 2004006860 A2 | 1/2004 |
| WO | 2004090546 A1 | 10/2004 |
| WO | 2006018315 A1 | 2/2006 |
| WO | 2009137113 A2 | 11/2009 |

OTHER PUBLICATIONS

Morgenthaler, NG, et al., Assay for the Measurement of Copeptin, a Stable Peptide Derived from the Precursor of Vasopressin, Clinical Chemistry, 52:1, 2006, pp. 112-119.
Morgenthaler, NG, et al., Copeptin: clinical use of a new biomarker, Trends in Endocrinology and Metabolism, vol. 19, No. 2, 2007, pp. 43-49.
Fenske, W., et al., Copeptin in the Differential Diagnosis of Hyponatremia, J Clin Endocrinol Metab, Jan. 2009, 94 (1):123-129.
Robertson GL, et al., Development and Clinical Application of a New Method for the Radioimmunoassay of Arginine Vasopressin in Human Plasma, The Journal of Clinical Investigation, vol. 52, Sep. 1973, pp. 2340-2352.
Kluge, M, et al., Improved Extraction Procedure and RIA for Determination of Arginine-8-Vasopressin in Plasma: Role of Premeasurement Sample Treatment and Reference Values in Children, Clinical Chemistry, vol. 45:1, 1999, pp. 98-103.
Preibisz, JJ, et al., Plasma and Platelet Vasopressin in Essential Hypertension and Congestive Heart Failure, 1982 Blood Pressure Council, Supp. I, Hypertension, vol. 5, No. 2, Mar.-Apr. 1983, pp. I-129-I-138.

(Continued)

*Primary Examiner* — Christine Foster
(74) *Attorney, Agent, or Firm* — Wood Herron & Evans LLP

(57) ABSTRACT

Method of obtaining and/or verifying a binder to prepro-Vasopressin (SEQ ID NO. 1) or fragments thereof of at least 6 amino acids in length, including Copeptin (SEQ ID NO. 2), comprising at least one of the steps of: a) generating the binder using a developer comprising an amino acid sequence of at least 6 amino acids in length contained in an amino acid sequence corresponding to the C-terminal part but lacking amino acid 164 of prepro-Vasopressin (SEQ ID NO. 1); b) determining whether the binder is capable of binding to an amino acid sequence of at least 4 amino acids in length contained in an amino acid sequence corresponding to the C-terminal part but lacking amino acid 164 of prepro-Vasopressin (SEQ ID NO. 1); c) selecting and optionally isolating the binder from a plurality of binders which is capable of binding to an amino acid sequence contained in an amino acid sequence corresponding to the C-terminal part but lacking amino acid 164 of prepro-Vasopressin (SEQ ID NO. 1); d) carrying out binding assays with the binder in order to determine the ex vivo stability of prepro-Vasopressin or fragments thereof of at least 6 amino acids in length, including Copeptin, in a biological sample; e) carrying out binding assays with the binder and another binder for comparison purposes in order to determine the concentration of prepro-Vasopressin or fragments thereof of at least 6 amino acids in length, including Copeptin, in a biological sample; wherein the C-terminal part consists of amino acids 138 to 164 of prepro-Vasopressin (SEQ ID NO. 1), in order to obtain a binder or a mixture of binders capable of binding to an epitope contained in an amino acid sequence corresponding to amino acids 138 to 163 but lacking amino acid 164 of prepro-Vasopressin (SEQ ID NO. 1).

2 Claims, 6 Drawing Sheets

Figure 1:
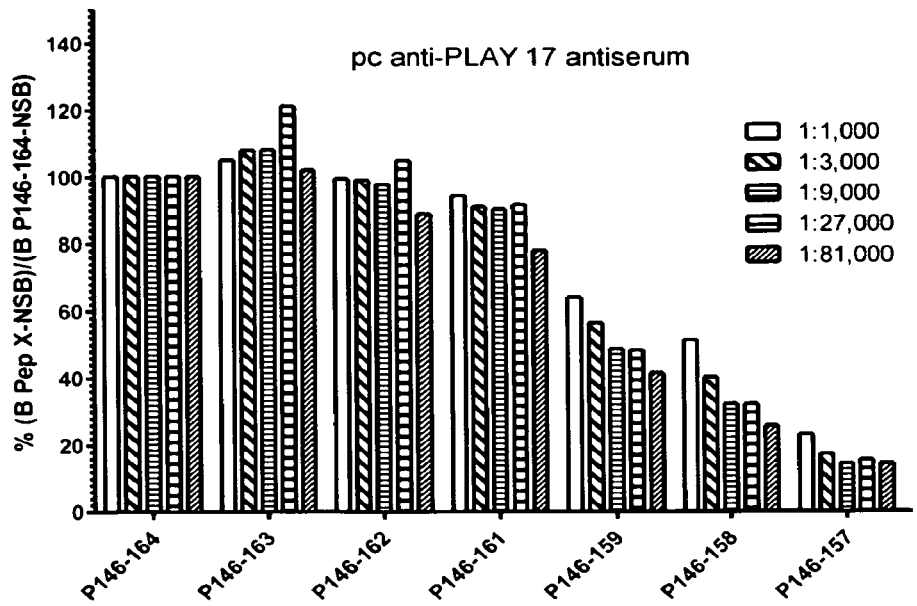
Figure 1:
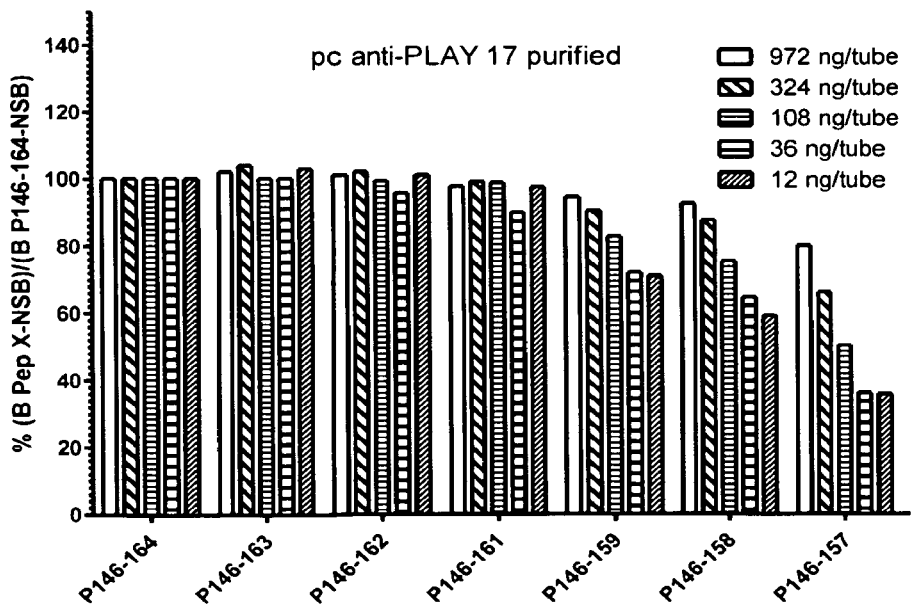
Figure 1:
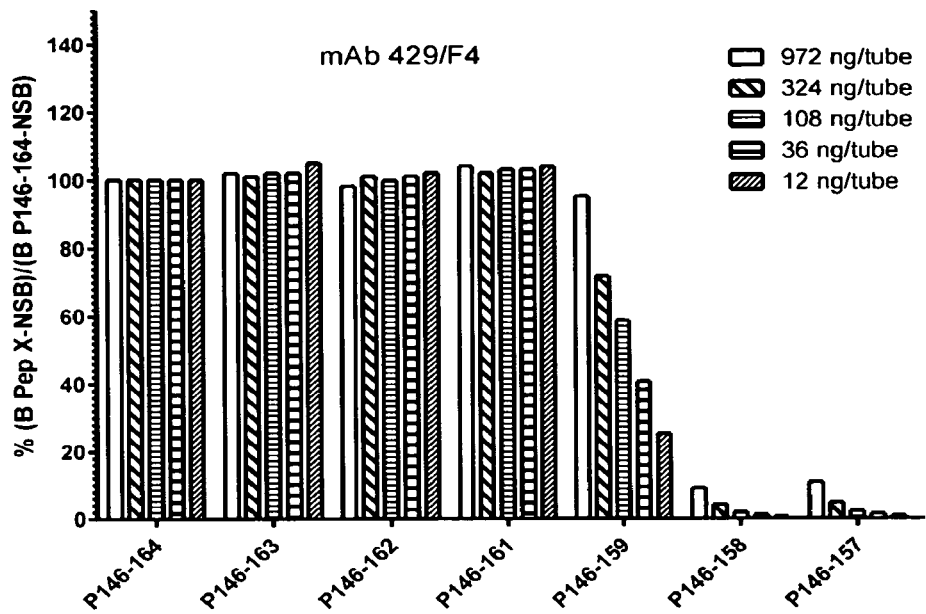
Figure 1:
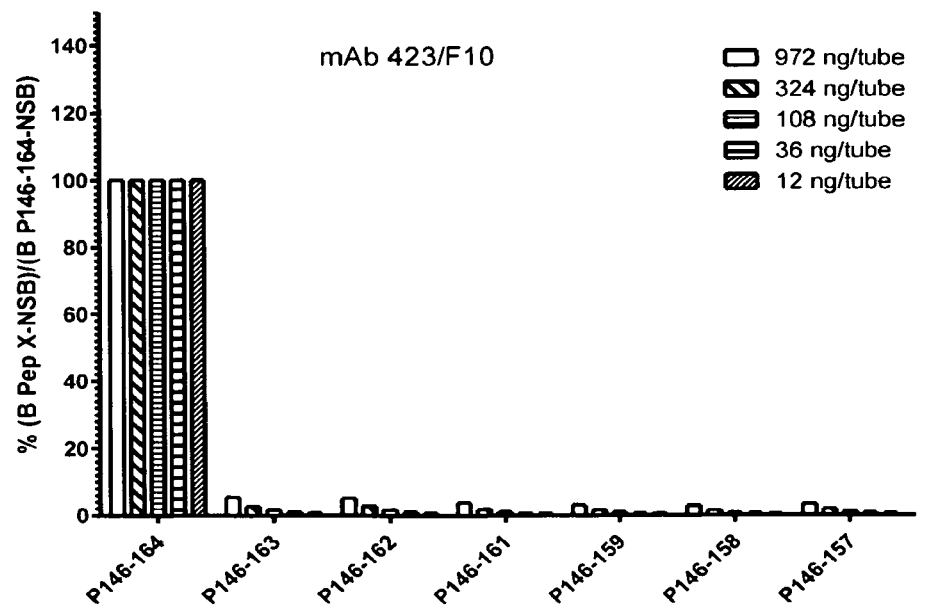

Specification includes a Sequence Listing.

(56) References Cited

OTHER PUBLICATIONS

International Searching Authority, International Search Report and Written Opinion in corresponding Application No. PCT/EP2012/002697, dated Oct. 2, 2012 (13 pages).
Struck, Joachim, et al, Copeptin, A Stable Peptide Derived From the Vasopressin Precursor, Is Elevated in Serum of Sepsis Patients, Peptides, Dec. 1, 2005, pp. 2500-2504, vol. 26, issue No. 12, Elsevier.
Harlow, E and Lane, D., Antibodies: A Laboratory Manual (1988) Cold Spring Harbor Laboratory Press, Cold Spring Harbor, NY pp. 72-78.
Hultschig, C. et al., Curr Opin Chem Biol. Feb. 2006;10(1):4-10. PMID: 16376134.
Lane, R.D., A short-duration polyethylene glycol fusion technique for increasing production of monoclonal antibody-secreting hybridomas. J Immunol Methods 1985; 81:223-8.
Wild, D., The Immunoassay Handbook, Ed., Elsevier LTD, Oxford; 3rd ed. (May 2005), ISBN-13: 978-0080445267 (Abstract). (one page).

METHOD OF OBTAINING A BINDER TO PREPRO-VASOPRESSIN OR FRAGMENTS THEREOF

CROSS-REFERENCE TO RELATED APPLICATION

This application is divisional application of U.S. application Ser. No. 14/127,656, filed Jun. 24, 2014 which claims priority to a submission under 35 U.S.C. § 371 of International Application No. PCT/EP2012/002697, filed Jun. 26, 2012, which claims priority to European Application No. 11005371.7, filed Jun. 30, 2011, the disclosures of which are hereby expressly incorporated by reference herein in their entireties.

The present invention relates to a method of obtaining and/or verifying a binder to prepro-Vasopressin (SEQ ID NO. 1) or fragments thereof, including Copeptin (SEQ ID NO. 2), a binder and a kit comprising the binder for qualitatively or quantitatively detecting prepro-Vasopressin (SEQ ID NO. 1) or fragments thereof, including Copeptin (SEQ ID NO. 2), in a biological sample, and a peptide for generating a binder to prepro-Vasopressin (SEQ ID NO. 1) or fragments thereof, including Copeptin (SEQ ID NO. 2).

BACKGROUND OF THE INVENTION

Prepro-Vasopressin (SEQ ID NO. 1) can be processed to Pro-Vasopressin by cleavage of the signal peptide, which can be further processed into Vasopressin, Neurophysin-2 and Copeptin (SEQ ID NO. 2), the latter representing the C-terminal moiety of the precursor peptide. Vasopressin, also known as antidiuretic hormone (ADH), is a key regulator of water and electrolyte balance. The measurement of Vasopressin in biological samples is barely possible in clinical routine due to considerable technical challenges related to its rapid clearance from the circulation, interaction with platelets in the serum, and small size, see "Literature", paragraph [0039], [1-3]. Copeptin (SEQ ID NO. 2), which is stoichiometrically formed together with Vasopressin, has been successfully established as a surrogate marker for Vasopressin. A major reason for this success is considered its extremely high ex vivo stability, making it suitable for routine use [4-6].

Clinical research has revealed numerous indications, where measurement of Copeptin (SEQ ID NO. 2) gives highly useful diagnostic information, including cardiological, pulmonological, infectious, kidney diseases, pathological disturbances of the water and electrolyte balance, and others [5]. Published methods for the detection of Copeptin (SEQ ID NO. 2) are immunoassays [4, 6].

Prepro-Vasopressin (SEQ ID NO. 1) and fragments thereof can be expressed also ectopically in certain types of cancer, and anti-Copeptin (SEQ ID NO. 2) antibodies can be used to detect expression in tissue samples (EP 1539818 A2).

While immunogens for the generation of anti-Copeptin (SEQ ID NO. 2) antibodies have been described, little, if any, is known about the actual epitopes of these antibodies. Described anti-human Copeptin (SEQ ID NO. 2) antibodies are listed in table 1. In the prior art, no attention has been paid to the question on whether and how the epitope specificity of anti-Copeptin (SEQ ID NO. 2) antibodies might affect the accuracy and robustness of the detection of prepro-Vasopressin (SEQ ID NO. 1) or fragments thereof including Copeptin (SEQ ID NO. 2) in biological samples, using such antibodies. It is rather generally believed that Copeptin (SEQ ID NO. 2) is very stable per se. An antibody for detection of mature Copeptin (SEQ ID NO. 2), the epitope of which is rather unspecifically defined as having been mapped "near the C-terminus of Copeptin" (SEQ ID NO. 2), is offered by Santa Cruz Biotechnology, Inc., Heidelberg, Germany, and recommended for use in ELISA and other applications.

TABLE 1

| Antibody | Origin | Immunogen | Epitope | Reference |
| --- | --- | --- | --- | --- |
| Anti-PATV17 | Sheep | CATQLDGPAGALLLRLV (SEQ ID NO: 14) representing positions 132-147 of pre-pro-Vasopressin (SEQ ID NO. 1) plus an N-terminal cystein residue | Not described | [6] |
| Anti-PLAY17 | Sheep | CLAGAPEPFEPAQPDAY (SEQ ID NO: 15) representing positions 149-164 of pre-pro-Vasopressin (SEQ ID NO. 1) plus an N-terminal cystein residue | Not described | [6] |
| 294/1A7 | Mouse | ATQLDGPAGALLLRLVQLAGAPEPFEPAQPDAY (SEQ ID NO. 16) representing positions 132-164 of pre-pro-Vasopressin (SEQ ID NO. 1) plus an N-terminal cystein residue | GPAGAL (SEQ ID NO. 20) representing positions 137-144 of pre-pro-Vasopressin (SEQ ID NO. 1) | WO 2010049179 A1 |
| H-065-32 | Rabbit | ASDRSNATQLDGPAGALLLRLVQLAGAPEPFEPAQPDAY (SEQ ID NO. 17) representing positions 126-164 of prepro-Vasopressin (SEQ ID NO. 1) | Not described | Phoenix Pharmaceuticals, Burlingame, USA |
| MAB607 7 (clone 579021) | Mouse | ASDRSNATQLDGPAG (SEQ ID NO. 18) representing positions 126-140 of pre-pro-Vasopressin (SEQ ID NO. 1) | Not described | R + D Systems, Minneapolis, USA |
| MAG-1 | Mouse | QLAGAPEPFEPAQPDAY (SEQ ID NO. 19) representing positions 148-164 of pre-pro-Vasopressin (SEQ ID NO. 1) | Not described | EP 1539818 A2 |

TABLE 1-continued

| Antibody | Origin | Immunogen | Epitope | Reference |
|---|---|---|---|---|
| sc-7811 | Goat | Not described | "epitope mapping near the C-terminus of Copeptin [(SEQ ID NO. 2)] of human origin" | Santa Cruz Biotechnology, Inc., Heidelberg, Germany |

DESCRIPTION OF THE INVENTION

Aspects of the present invention relate to a method of obtaining and/or verifying a binder to prepro-asopressin or fragments thereof. Aspects of the present invention also relate to a monoclonal antibody capable of binding to an epitope contained in an amino acid sequence of the C-terminal part of prepro-vasopressin. Further aspects of the present invention relate to a cell line producing a monoclonal antibody capable of binding to an epitope contained in an amino acid sequence of the C-terminal part of prepro-vasopressin.

In detail, in a first aspect, the invention concerns a method of obtaining and/or verifying a binder to prepro-Vasopressin (SEQ ID NO. 1) or fragments thereof of at least 6 amino acids in length, including Copeptin (SEQ ID NO. 2), comprising at least one of the steps of:
a) generating the binder using a developer comprising an amino acid sequence of at least 6 amino acids in length contained in an amino acid sequence corresponding to the C-terminal part but lacking amino acid 164 of prepro-Vasopressin (SEQ ID NO. 1);
b) determining whether the binder is capable of binding to an amino acid sequence of at least 4 amino acids in length contained in an amino acid sequence corresponding to the C-terminal part but lacking amino acid 164 of prepro-Vasopressin (SEQ ID NO. 1);
c) selecting and optionally isolating the binder from a plurality of binders which is capable of binding to an amino acid sequence contained in an amino acid sequence corresponding to the C-terminal part but lacking amino acid 164 of prepro-Vasopressin (SEQ ID NO. 1);
d) carrying out binding assays with the binder in order to determine the ex vivo stability of prepro-Vasopressin (SEQ ID NO. 1) or fragments thereof of at least 6 amino acids in length, including Copeptin (SEQ ID NO. 2), in a biological sample;
e) carrying out binding assays with the binder and another binder for comparison purposes in order to determine the concentration of prepro-Vasopressin (SEQ ID NO. 1) or fragments thereof of at least 6 amino acids in length, including Copeptin (SEQ ID NO. 2), in a biological sample;
wherein the C-terminal part consists of amino acids 138 to 164 of prepro-Vasopressin (SEQ ID NO. 1),
in order to obtain a binder or a mixture of binders capable of binding to an epitope contained in an amino acid sequence corresponding to amino acids 138 to 163 but lacking amino acid 164 of prepro-Vasopressin (SEQ ID NO. 1).

The main aspect of the present invention is the surprising finding that fragments of prepro-Vasopressin (SEQ ID NO. 1) and especially Copeptin (SEQ ID NO. 2) in biological samples are not extremely stable per se, as the prior art suggests, but that analyte stability and the accurate and reliable detection depend on the epitope against which antibodies used in an assay to detect the fragments, such as Copeptin (SEQ ID NO. 2), are directed. In particular, it was found that the exclusion of amino acid position 164 in the C-terminal portion of prepro-Vasopressin (SEQ ID NO. 1) as part of the epitope for a binder to prepro-Vasopressin (SEQ ID NO. 1) or fragments thereof, such as Copeptin (SEQ ID NO. 2), is highly critical concerning both, accurate detection and analyte stability. Accordingly, the method comprises steps making sure to find those binders which do not require the presence of amino acid 164 in the epitope of an amino acid sequence corresponding to the C-terminal part of prepro-Vasopressin (SEQ ID NO. 1), i.e., the amino acid sequence starting with and downstream of amino acid 138. As was found and confirmed in the present invention, binders not requiring amino acid 164 in the epitope for binding lead to more accurate and reliable analytical results and are thus more suited to be used in assays for detecting prepro-Vasopressin (SEQ ID NO. 1) or fragments thereof than the binders needing said amino acid 164 for binding.

It could further be shown that not only amino acid 164 may be lacking from the C-terminal portion of prepro-Vasopressin (SEQ ID NO. 1) as part of the epitope for a binder to prepro-Vasopressin (SEQ ID NO. 1) or fragments thereof but that improved results may also be obtained when more than the one amino acid is missing. In more detail, amino acids 163 and 164, preferably 162-164 and most preferably amino acids 161-164 may be lacking from the amino acid sequence corresponding to the C-terminal part of prepro-Vasopressin (SEQ ID NO. 1). That is, the binder obtainable by the method of the invention does not require the presence of these amino acids in the epitope for binding to prepro-Vasopressin (SEQ ID NO. 1) or fragments thereof, including Copeptin (SEQ ID NO. 2).

The terms "prepro-Vasopressin" (SEQ ID NO. 1) and "Copeptin" (SEQ ID NO. 2) as used herein comprise also amino acid sequences showing e.g. only 75% homology, preferred at least 80% homology, more preferred at least 90% homology to prepro-Vasopressin (SEQ ID NO. 1) and Copeptin (SEQ ID NO. 2), respectively. The same applies to other fragments of prepro-Vasopressin (SEQ ID NO. 1) than Copeptin (SEQ ID NO. 2). "Fragments" of prepro-Vasopressin (SEQ ID NO. 1) relate to fragments of at least 6 amino acids in length, preferably at least 8, especially preferably at least 10 and most preferably at least 12 amino acid residues in length.

The method of the invention describes several ways of obtaining and/or verifying suitable binders not needing amino acid 164 for binding, as described above, which may be employed solely or in combination with each other. A first possibility is given in step a) and concerns the purposeful and selective generation of the binder by using a suitable developer selectively leading to the desired binder. Concretely, the developer comprises an amino acid sequence contained in an amino acid sequence corresponding to the C-terminal part but lacking amino acid 164 of prepro-Vasopressin (SEQ ID NO. 1). That is, the developer comprises an amino acid sequence of at least 6 amino acids in length which corresponds to at least a part of the amino acid sequence from amino acids 138 to 164 of prepro-Vasopressin (SEQ ID NO. 1) but does not have amino acid 164. Using a developer wherein amino acid 164 is missing in the amino acid sequence leads to a binder or a mixture of binders not requiring said amino acid 164 for binding. (In the following, the term "binder" shall mean both a single type of binder or a mixture of different types of binders, unless otherwise stated.) Principally, step a) thus selectively and directly leads to the desired binder and does not require additional steps in order to remove binders needing said amino acid 164 for binding. However, this does not exclude that, after step a), additional steps, such as characterization, purification, selection and isolation steps, may follow.

In the context of this invention, the amino acid sequence contained in an amino acid sequence corresponding to the C-terminal part but lacking amino acid 164 of prepro-Vasopressin (SEQ ID NO. 1) used for generating the binder can principally be a synthetically prepared or naturally derived amino acid sequence. It may be linear or folded. The said amino acid sequence may principally be of any length of 6 or more amino acids suitable for generating the desired binder or for obtaining efficient binding to the binder. It may principally correspond to any amino acid sequence between amino acids 138 and 163 of prepro-Vasopressin (SEQ ID NO. 1). Preferably, the amino acid sequence is contained in the sequence of amino acids 140 to 163 (SEQ ID NO. 21), more preferably 142 to 163 (SEQ ID NO. 22), especially preferably 144 to 163 (SEQ ID NO. 23) and most preferably 146 to 163 (SEQ ID NO. 7) of prepro-Vasopressin (SEQ ID NO. 1). Suitably, the amino acid sequence has at least 8, preferably at least 10 and most preferably at least 12 amino acids. Particularly, said amino acid sequence contains at least 6, preferably at least 8, more preferably at least 10 and most preferably at least 12 consecutive amino acids contained in the amino acid sequence corresponding to amino acids 146 to 163 of prepro-Vasopressin (SEQ ID NO. 1).

As used herein, the term "binder" refers to any substance capable of binding to an epitope contained in an amino acid sequence corresponding to the C-terminal part of prepro-Vasopressin (SEQ ID NO. 1). This binder is generally shaped adequately, both spatially and in terms of surface features, such as surface charge, hydrophobicity, hydrophilicity, presence or absence of Lewis donors and/or acceptors, to specifically bind the target molecules or molecules of interest, i. e., prepro-Vasopressin (SEQ ID NO. 1) or fragments thereof, including Copeptin (SEQ ID NO. 2). Hereby, the binding may for instance be mediated by ionic, van-der-Waals, pi-pi, sigma-pi, hydrophobic or hydrogen bond interactions or a combination of two or more of the aforementioned interactions between the binder and the target molecules or molecules of interest. Such binders may be selected from but are not limited to the group consisting of antibodies and aptamers.

Preferably, the binder is an antibody, preferably a monoclonal antibody, polyclonal antiserum, enriched or purified polyclonal antibody, recombinant antibody, or a functional derivative thereof. The term "antibody" as used herein, unless indicated otherwise, is used broadly to refer to both, antibody molecules and a variety of antibody-derived molecules. Such antibody-derived molecules comprise at least one variable region (either a heavy chain or a light chain variable region), as well as individual antibody light chains, individual antibody heavy chains, chimeric fusions between antibody chains and other molecules, and the like. Functional immunoglobulin fragments according to the present invention may be Fv, scFv, disulfide-linked Fv, Fab, and F(ab')2. Also encompassed by the term "antibody" are polyclonal antibodies, monoclonal antibodies, preferably IgG1 antibodies; chimeric monoclonal antibodies; humanized antibodies, genetically engineered monoclonal antibodies. Functional derivatives are chemically and/or biochemically modified variants of the antibodies/antisera having an analogous functionality/binding capacity. Analogously, the developer may be any substance suited for generating a binder of the invention. Preferably, the developer is an immunogen, most preferably a—natural or synthetic—peptide, comprising an amino acid sequence of at least 6 amino acids in length contained in the amino acid sequence corresponding to the C-terminal part of prepro-Vasopressin (SEQ ID NO. 1).

The term "developer" as used herein refers to a binding-site related substance for the generation of a binder, e.g. an amino acid sequence. The developer may consist of the amino acid sequence as described above or may contain this amino acid sequence as the functional part of the compound. For example, the developer may additionally comprise a linking part, such as another amino acid sequence. Preferably, the developer is selected from the group comprising the peptides consisting of amino acids 146-163 (SEQ ID NO. 7), 146-162 (SEQ ID NO. 8), 146-161 (SEQ ID NO. 9), 146-160 (SEQ ID NO. 10), 146-159 (SEQ ID NO. 11), 146-158 (SEQ ID NO. 12) and 146-157 (SEQ ID NO. 13) of prepro-Vasopressin (SEQ ID NO. 1). These peptides and their use in the method of the invention are also part of the present invention. The methods of raising binders, particularly antibodies, using peptides are generally known in the art as thus need not be described here.

In step b) of the instant invention it is determined whether the binder is capable of binding to an amino acid sequence contained in an amino acid sequence corresponding to the C-terminal part but lacking amino acid 164 of prepro-Vasopressin (SEQ ID NO. 1). Here, and also in step c), the amino acid sequences and the C-terminal part are defined as in step a) above, with the exception that a length of at least 4 amino acids in the amino acid sequence is regarded as sufficient for determining binding. Preferably, the amino acid sequence has at least 6, more preferably at least 8, even more preferably at least 10 and most preferably at least 12 consecutive amino acids contained in the amino acid sequence corresponding to amino acids 146 to 163 (SEQ ID NO. 7) of prepro-Vasopressin (SEQ ID NO. 1), and preferably is an amino acid sequence selected from the group consisting of amino acids 146-163 (SEQ ID NO. 7), 146-162 (SEQ ID NO. 8), 146-161 (SEQ ID NO. 9), 146-160 (SEQ ID NO. 10), 146-159 (SEQ ID NO. 11), 146-158 (SEQ ID NO. 12) and 146-157 (SEQ ID NO. 13) of prepro-Vasopressin (SEQ ID NO. 1).

Step b) may, for example, be used in addition to step a) in order to verify the suitability of the binder obtained in the generating step. However, more preferably, step b) may be used in order to find out whether a binder, which has not been prepared using a selective developer as in step a) and where it is not clear whether it will need said amino acid 164 in the epitope for binding, is actually capable of binding to an amino acid sequence of at least 4 amino acids in length contained in an amino acid sequence corresponding to the C-terminal part but lacking amino acid 164 of prepro-Vasopressin (SEQ ID NO. 1). This also applies to mixtures of binders where it may be necessary to find out whether it contains binders which require amino acid 164 in the epitope for effective binding. If this is confirmed these undesired binders may then be removed in a later step.

Step b) can be carried out using any suitable determining method known to the expert. A preferred way of determining whether the binder is capable of binding to an amino acid sequence of at least 4 amino acids in length corresponding to the amino acid sequence of the C-terminal part of prepro-Vasopressin (SEQ ID NO. 1) is epitope mapping. Epitope mapping is a process known to a person skilled in the art. Epitope mapping is the process of identifying the binding sites, or "epitopes", of binders on their target antigens. There are two types of general structures that binders use to bind antigens: linear and conformational. Linear epitopes are formed by a continuous sequence of amino acids in a protein, while conformational epitopes are composed of amino acids that are discontinuous in the protein sequence but are brought together upon three-dimensional protein folding. There are several methods available for mapping binding epitopes on target antigens. The gold standard approach is X-ray co-crystallography, which allows direct visualization of the interaction between the antigen and the binder. However, this approach is technically challenging, requires large amounts of purified protein, and can be time-consuming and expensive. An alternative approach for epitope mapping is peptide scanning. This technique uses a library of short peptide sequences from overlapping segments of a target protein and tests for their ability to bind the antibody of interest. This method is faster and relatively inexpensive, but is primarily used for mapping linear, not conformational, epitopes. In order to test whether the binder is capable of binding to the respective amino acid sequence, the amino acid sequence can be bound directly or indirectly to a solid phase. For indirect binding the amino acid sequence may contain this amino acid sequence as the functional part of the compound. For example, the amino acid sequence may additionally comprise a linking part, such as biotin. Biotinylated amino acid sequences can be immobilized via streptavidin, avidin, neutravidin or captavidin that is bound directly on the solid phase. As biotin binds with an extremely high affinity and specificity to streptavidin, avidin, neutravidin or captavidin, the amino acid sequence that has to be tested for binding of the respective binder is consequently indirectly bound to the solid phase via a biotin/streptavidin-complex. Another approach for epitope mapping is site-directed mutagenesis. Using this approach, systematic mutations of amino acids are introduced into a protein sequence followed by measurement of specific binding of the binder in order to identify amino acids that comprise an epitope. This technique has the advantage of mapping both linear and conformational epitopes, but is labor-intensive and slow, typically limiting analysis to a small number of amino acid residues. All these methods can be used in step b) of the invention. Preferably, however, in this process, binding of the binder against variants of the binding region is assessed. Such variants may be truncated, mutated, extended or otherwise modified representations of the binding region, which are typically produced by chemical synthesis or as recombinant peptides/proteins by molecular biological methods. It has to be noted that the interpretation of experimental epitope mapping data may be strongly influenced by the experimental conditions applied, such as for instance the amount of binding targets offered, concentrations of binder applied, applied detection method, applied incubation conditions etc. This is however known to the expert and can thus be taken into account.

If it has turned out—for example, in the determining step b) described above—that a mixture of binders was obtained, or if it is clear that the preparation method leads to a mixture of binders, and the mixture contains undesired binders which require amino acid 164 in the epitope for effective binding, these undesired binders should be removed or at least depleted. For this purpose, the method of the invention comprises step c) in which the desired binder not requiring amino acid 164 of prepro-Vasopressin (SEQ ID NO. 1) in the epitope for binding and thus leading to improved analytical results is selected so that it may be separated from the undesired binder. This selecting step may be any process suited to selectively get hold of the desired binder in order to enrich it compared with the undesired binder. A preferred way to do so is affinity separation. This method uses the different binding properties of the molecules to be separated. The most common process is affinity chromatography wherein a ligand specific for the binding site of the target molecule is coupled to an inert chromatography matrix. Under binding conditions this specific ligand on the chromatography matrix will bind molecules according to its specificity only. All other sample components will pass unbound through the chromatography medium. After a wash step the bound molecules may then be released and eluted by changing the conditions towards dissociation or by adding an excess of a substance that displaces the target molecule from the affinity ligand (competitive elution). The binder can thus be isolated in purified form. The invention is, however, not restricted to the above selection, purification and isolating steps, but any other suitable methods can also be employed.

Finding out whether a binder requires amino acid 164 of prepro-Vasopressin (SEQ ID NO. 1) in the epitope for binding may also be accomplished by carrying out binding assays, according to steps d) and e) of the invention. Both steps indirectly characterize the epitope specificity of the binder and are thus steps verifying the suitability of the binder.

As mentioned herein, an "assay" can be of any type applied in the field of diagnostics. Such an assay may be based on the binding of an analyte to be detected to one or more capture probes with a certain affinity. Concerning the interaction between capture molecules and target molecules or molecules of interest, the affinity constant is preferably greater than $10^8$ $M^{-1}$. "Capture molecules" are molecules which may be used to bind target molecules or molecules of interest. The capture molecules must thus be shaped adequately, both spatially and in terms of surface features, such as surface charge, hydrophobicity, hydrophilicity, presence or absence of Lewis donors and/or acceptors, to specifically bind the target molecules or molecules of interest. As mentioned before, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest.

The assays can have various formats, such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13: 978-0080445267; Hultschig C et al., Curr Opin Chem Biol. 2006 February; 10(1):4-10. PMID: 16376134, incorporated herein by reference).

In a particularly preferred embodiment the assay comprises two capture molecules, preferably antibodies which are both present as dispersions in a liquid reaction mixture, wherein a first labeling component is attached to the first capture molecule, wherein said first labeling component is part of a labeling system based on fluorescence- or chemiluminescence-quenching or amplification, and a second labeling component of said marking system is attached to the second capture molecule, so that upon binding of both capture molecules to the analyte a measurable signal is generated that allows for the detection of the formed sandwich complexes in the solution comprising the sample.

Even more preferred, said labeling system comprises rare earth cryptates or rare earth chelates in combination with fluorescence dye or chemiluminescence dye, in particular a dye of the cyanine type.

In step d), a binding assay is carried out with the binder in order to determine the ex vivo stability of prepro-Vasopressin (SEQ ID NO. 1) or fragments thereof, including Copeptin (SEQ ID NO. 2), in a biological sample. As has been shown in the present invention, the analyte stability is higher when a binder is used not requiring amino acid 164 of prepro-Vasopressin (SEQ ID NO. 1) or its fragment for binding compared to those binders needing said amino acid 164 for binding. Consequently, the analyte stability can be used to make conclusions regarding the type of binder. Those analytes having the highest stability are those not requiring amino acid 164 for binding and are thus the binders preferred in the present invention. Binders already known not to require amino acid 164 for binding can be used for comparison purposes, i.e., the analyte stability related to these comparison binders can be used as a standard with which the analyte stability evaluated for new binders is compared.

Step e), which may be used as an alternative or additional to step d), also uses another binder for comparison purposes, and binding assays are carried out with this binder for comparison purposes and the new binder in order to determine the concentration of prepro-Vasopressin (SEQ ID NO. 1) or fragments thereof, including Copeptin (SEQ ID NO. 2), in a biological sample. The binder for comparison purposes suitably is a binder already known to not require said amino acid 164 of prepro-Vasopressin (SEQ ID NO. 1) for binding to the said epitope. A new binder also not needing said amino acid 164 of prepro-Vasopressin (SEQ ID NO. 1) in the epitope for binding is expected to give results with similar or higher concentrations of prepro-Vasopressin (SEQ ID NO. 1) or fragments thereof, including Copeptin (SEQ ID NO. 2), in a biological sample as the binder for comparison purposes, while binders requiring said amino acid 164 are expected to result in lower concentrations.

As already mentioned above, the method of the invention may be comprised of only one of steps a) to e). For example, it may consist solely of step a), step b), step c), step d) or step e). The method, however, also encompasses combinations of two or more of steps a) to e) in any suitable order. For example, a preparation step suspected to having resulted in a mixture containing both desired and undesired binders may be followed by an analyzing step, such as step b), d) or e), which may then optionally be followed by selecting the desired binders in accordance with step c) and then, if so desired, by an isolating step resulting in the enriched desired binder (which, as mentioned above, may also be a mixture of desired binders).

With the method of the invention, employing at least one of the method steps a) to e), it is possible to obtain those binders capable of efficiently binding to an epitope contained in an amino acid sequence corresponding to amino acids 138 to 163 but lacking amino acid 164 of prepro-Vasopressin (SEQ ID NO. 1), which, as the invention has surprisingly shown, are those binders which do not require the presence of amino acid 164 in the epitope of an amino acid sequence corresponding to the C-terminal part of prepro-Vasopressin (SEQ ID NO. 1) for effective binding. As a result, more reliable analytical results can be obtained when using the binder, which is obtainable by the method of the invention, or a kit comprising said binder for qualitatively or quantitatively detecting prepro-Vasopressin (SEQ ID NO. 1) or fragments thereof, including Copeptin (SEQ ID NO. 2), in a biological sample.

The biological sample may be any kind of bodily fluid and is preferably selected from the group comprising blood, serum, plasma, urine, cerebrospinal fluid and saliva. Preferably, the sample is a blood sample, most preferably a serum sample or a plasma sample. Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e. g. citrated, EDTA or heparinized blood) for at least 15 minutes at 2000 to 3000 g. Therefore, it is preferred that plasma samples employed in the context of the present invention have been subjected to centrifugation at more than 1500 g for 30 min, preferably at least at 2000 g for at least 30 min, more preferably at least at 3000 g for at least 20 min, most preferably at least at 3000 g for at least 30 min.

"Serum" in the context of the present invention is the undiluted, extracellular portion of blood after adequate coagulation is completed. Coagulation is usually completed after 30 min. Serum can be obtained by centrifugation of the coagulated sample for at least 10 minutes at a minimum speed of 1500 g. Therefore, it is preferred that serum samples employed in the context of the present invention have been subjected to centrifugation at least at 1500 g for at least 10 min, preferably for at least 15 min, more preferably for at least 20 min. Most preferably the serum sample has been subjected to a centrifugation at least at 3000 g for at least 20 min.

The reliability of the results in determining prepro-Vasopressin (SEQ ID NO. 1) or fragments thereof may be even more improved by using at least one other binder in addition to the binder of the invention. This other binder suitably binds to another epitope of prepro-Vasopressin (SEQ ID NO. 1) or its fragments than the binder of the invention. The epitope used by the other binder for binding preferably is an epitope fully or partially contained in an amino acid sequence corresponding to amino acids 126 to 164 of prepro-Vasopressin (SEQ. ID NO. 1). Especially preferably, the epitope is fully or partially contained in an amino acid sequence corresponding to amino acids 126 to 146 and most preferably in amino acids 126 to 137 of prepro-Vasopressin (SEQ ID NO. 1). "Partially contained" in this context means that only a part of the epitope lies within the amino acid sequence corresponding to amino acids 126 to 164 of prepro-Vasopressin (SEQ ID NO. 1) while the other part lies upstream, towards the N-terminal, of the amino acid sequence. That is, part of the epitope overlaps with said amino acid sequence of prepro-Vasopressin (SEQ ID NO. 1) while the rest of the epitope lies upstream thereof. The overlap preferably is at least 6 amino acids. The additional binder refers to any substance capable of binding to an epitope fully or partially contained in an amino acid sequence corresponding to amino acids 126 to 164 of prepro-Vasopressin (SEQ ID NO. 1). Preferably, the additional binder is an antibody, preferably a monoclonal antibody, polyclonal antiserum, enriched or purified polyclonal antibody, recombinant antibody, or a functional derivative thereof.

The invention will further be described with reference to the attached drawings and examples. The figures and examples relate to preferred embodiments of the invention but the invention is not restricted to these embodiments but comprises all other embodiments encompassed by the scope of the claims.

DRAWINGS

FIG. 1 Epitope mapping of anti-PLAY17 sheep antiserum (FIG. 1 (A)), affinity purified sheep polyclonal anti-PLAY17 antibody (FIG. 1 (B)), mAb 429/F4 (FIG. 1 (C)) and mAb 423/F10 (FIG. 1 (D)). Data are represented as binding obtained against the respective indicated peptide minus non-specific binding (that is binding obtained, when the antibody to be tested was omitted), relative to the binding obtained against the P146-164 (SEQ ID NO. 6) peptide minus non-specific binding. Results are shown for different dilutions/amounts of the antisera/antibodies tested.

Figure 2:
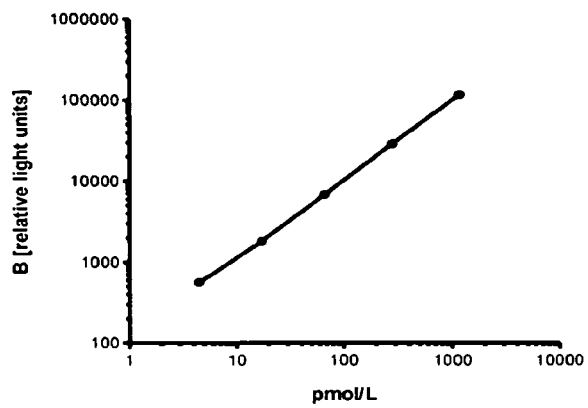
Figure 2:
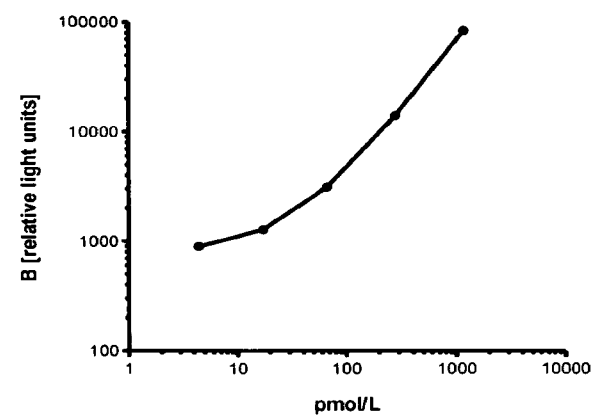
Figure 2:
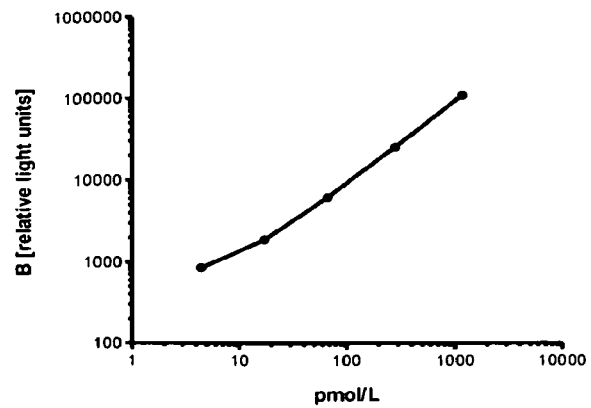

FIG. 2 Dose response curves for the assays Pc anti-PLAY17/mc anti-PATV17 (FIG. 2 (A)), mAb 429/F4/mc anti-PATV17 (FIG. 2 (B)), mAb 423/F10/mc anti-PATV17 (Fi. 2 (C)).

Figure 3:
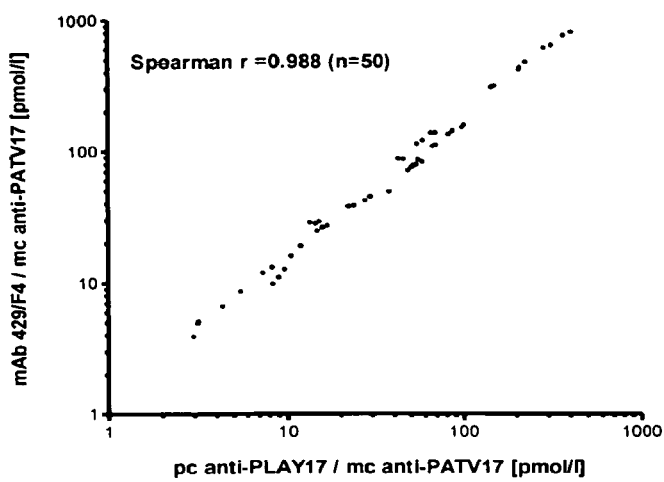
Figure 3:
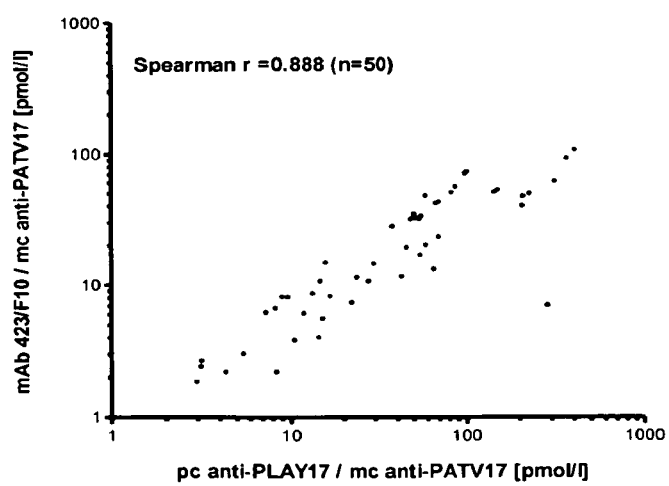
Figure 3:
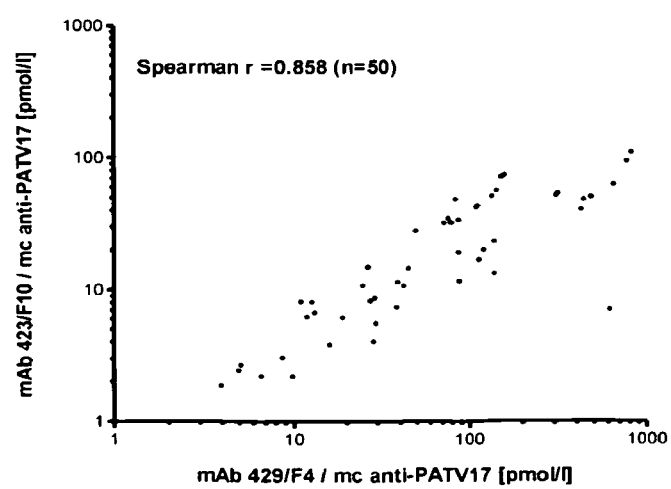

FIG. 3 Correlation of serum samples measured with Pc anti-PLAY17/mc anti-PATV17 and mAb 429/F4/mc anti-PATV17 (FIG. 3 (A)), Pc anti-PLAY17/mc anti-PATV17 and mAb 423/F10/mc anti-PATV17 (FIG. 3 (B)), mAb 423/F10/mc anti-PATV17 and mAb 429/F4/mc anti-PATV17 (FIG. 3 (C)).

Figure 4:
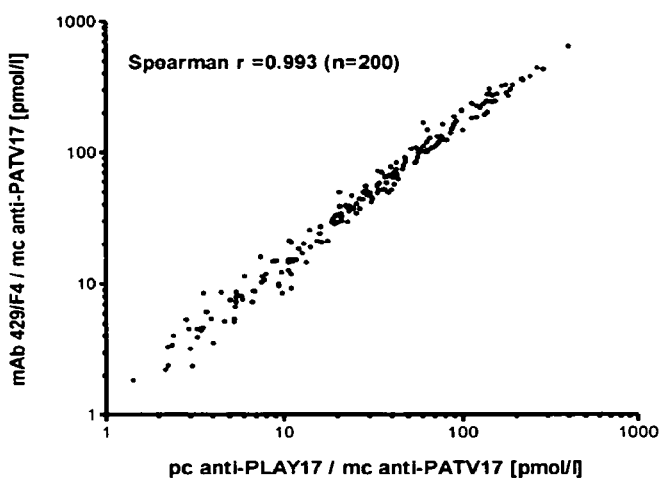
Figure 4:
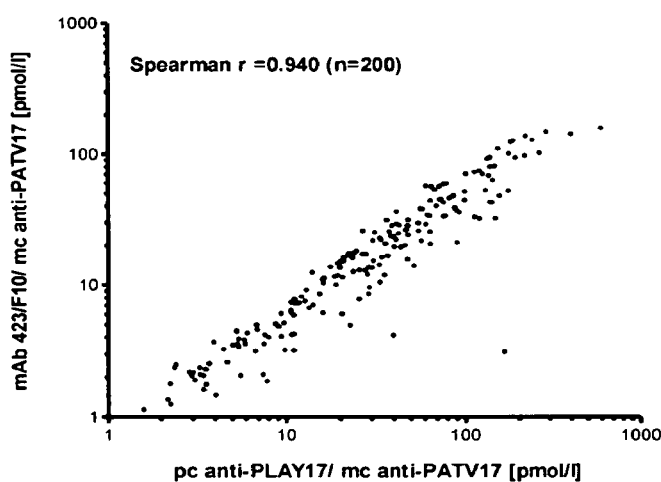
Figure 4:
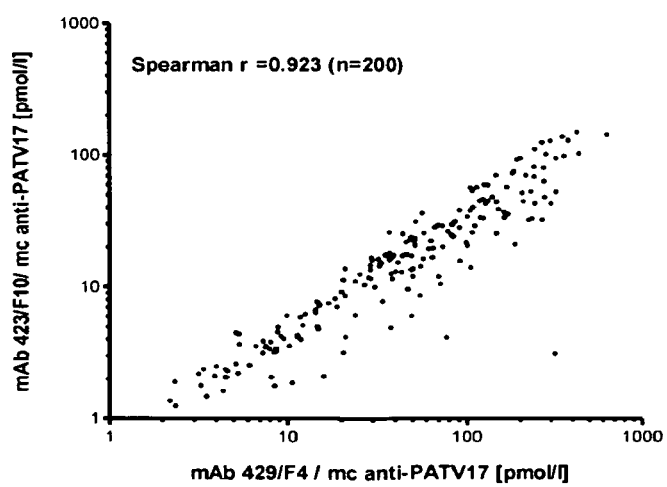

FIG. 4 Correlation of EDTA-plasma samples measured with Pc anti-PLAY17/mc anti-PATV17 and mAb 429/F4/mc anti-PATV17 (FIG. 4 (A)), Pc anti-PLAY17/mc anti-PATV17 and mAb 423/F10/mc anti-PATV17 (FIG. 4 (B)), mAb 423/F10/mc anti-PATV17 and mAb 429/F4/mc anti-PATV17 (FIG. 4 (C)).

Figure 5:
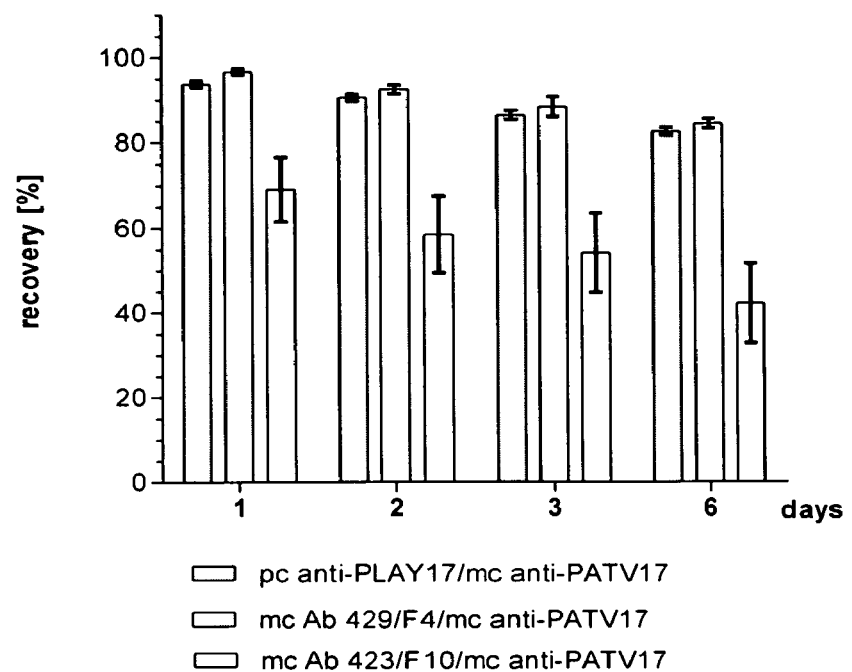

FIG. 5 Analyte stability. Shown are mean values (SEM) of five serum samples after storage at 22° C. for the indicated time periods in the relation to the values measured without having the samples stored (t=0), when samples were measured with the assays indicated.

EXAMPLES

Peptides

The following Copeptin (SEQ ID NO. 2)-related peptides were chemically synthesized, purified, and quality controlled employing standard procedures:

| Peptide | Sequence | SEQ ID NO. | Amino acid position of prepro-Vasopressin (SEQ ID NO. 1) |
|---|---|---|---|
| PAY16 | CAGAPEPFE PAQ PDAY | 4 | 150-164 (+ N-terminal Cystein) |
| PAY14 | CAPEPFE PAQ PDAY | 3 | 152-164 (+ N-terminal Cystein) |
| P146-164 | LVQLAGAPEPFEPAQPDAY | 6 | 146-164 |
| P146-163 | LVQLAGAPEPFEPAQPDA | 7 | 146-163 |
| P146-162 | LVQLAGAPEPFEPAQPD | 8 | 146-162 |
| P146-161 | LVQLAGAPEPFEPAQP | 9 | 146-161 |
| P146-159 | LVQLAGAPEPFEPA | 11 | 146-159 |
| P146-158 | LVQLAGAPEPFEP | 12 | 146-158 |
| P146-157 | LVQLAGAPEPFE | 13 | 146-157 |

Antibodies

Monoclonal antibodies directed against the peptides PAY16 (SEQ ID NO. 4) and PAY14 (SEQ ID NO. 3) were generated by standard procedures (Harlow E, Lane D. Antibodies—A Laboratory Manual. Cold Spring Harbor: Cold Spring Harbor Laboratory, 1988; Lane RD. A short-duration polyethylene glycol fusion technique for increasing production of monoclonal antibody-secreting hybridomas. J Immunol Methods 1985; 81:223-8.):

Briefly, peptides were conjugated to BSA by using Sulfo-MBS (m-maleimidobenzoyl-N-hydroxysuccinimid ester). With these conjugates Balb/c mice were immunized and boostered, and spleen cells were fused with SP2/0 myeloma cells to generate hybridoma cell lines. Cell lines were screened for their ability to secrete antibodies that would bind to the immunogenic peptides, which were coated on a solid polystyrene phase.

With this approach, cell lines secreting monoclonal antibodies 429/F4 (against PAY16 (SEQ ID NO. 4)) and 423/F10 (against PAY14 (SEQ ID NO. 3)) were generated. A hybridoma cell line producing the monoclonal antibody 429/F4 was deposited on Nov. 4, 2020 under Accession No. DSM ACC3364. The deposited hybridoma cell line that produces the monoclonal antibody 429/F4 has an identification reference in the depository of mcAB aPAY 16 429/F4. The name of the depository is Leibniz Institute DSMZ-German Collection of Microorganisms and Cell Cultures, having an address of Inhoffenstr. 7 B, D-38124 Braunschweig, Germany. For further experiments, monoclonal antibodies were purified from culture supernatant by Protein G affinity chromatography.

Sheep antiserum and corresponding affinity purified polyclonal sheep antibodies developed against peptide PLAY17 ("pc anti-PLAY"), used in chemiluminescence/coated tube assays to detect Copeptin (SEQ ID NO. 2) (CT-proAVP) as described [4, 7] were from BRAHMS GmbH, Hennigsdorf, Germany.

Epitope Mapping

The epitopes of the antibodies were mapped as follows:

a) Coating of Peptides

Coating was done by standard procedures (EP 1488209 A1, EP 1738178 A1): Polystyrene startubes (Greiner) were coated with peptides P146-164 (SEQ ID NO. 6), P146-163 (SEQ ID NO. 7), P146-162 (SEQ ID NO. 8), P146-161 (SEQ ID NO. 9), P146-159 (SEQ ID NO. 11), P146-158 (SEQ ID NO. 12) and P146-157 (SEQ ID NO. 13) (per tube, 1.5 µg of peptide in 300 µl of PBS, pH 7.8) overnight at 22° C. Tubes were then blocked with 10 mmol/L Na-phosphate (pH 6.5) containing 3% Karion FP (Merck), 0.5% BSA protease free (Sigma) and lyophilized.

b) Labeling of Donkey-Anti-Sheep IgG and Goat-Anti-Mouse IgG Antibodies

Labeling was done by standard procedures (EP 1488209 A1, EP 1738178 A1): The concentration of the donkey-anti-sheep (Scantibodies Laboratory Inc., USA) and goat-anti-mouse antibody (BiosPacific, USA) was adjusted to 1 g/L, and the antibodies were labeled by incubation with the chemiluminescent label MACN-Acridinium-NHS-Ester (1 g/L; InVent GmbH, Hennigsdorf, Germany) in a 1:4 molar ratio for 20 min at room temperature. The reactions were stopped by addition of 1/10 volume of 1 mol/L Tris for 10 min at room temperature. Labeled antibodies were separated from free label by size-exclusion chromatography on a NAP-5 column (GE Healthcare, Freiburg, Germany) and a Thermo BioBasic 300 5 µm HPLC column (Thermo Scientific).

c) Pc Anti-PLAY17 Antiserum/Affinity Purified Antibody

Tracer was produced by diluting the labeled donkey-anti-sheep IgG antibody in assay buffer PBS, 0.5% bovine serum albumin protease free (Sigma) containing 106 relative light units (RLU) of MACN-labeled antibody per 200 µl. Pc anti-PLAY17 sheep antiserum (B.R.A.H.M.S GmbH, Hennigsdorf, Germany) was diluted with PBS, 0.5% bovine serum albumin (protease free) at a ratio of 1:1000, 1:3000, 1:9000, 1:27000 and 1:81000. Affinity purified pc anti-PLAY17 sheep antibodies were diluted with PBS, 0.5% bovine serum albumin protease free to following concentrations: 972, 324, 108, 36 and 12 ng/200 µl. In the first incubation step 50 µl of the dilutions of pc anti-PLAY17 sheep antiserum/purified antibodies and 200 µl PBS, 0.5% bovine serum albumin (protease free) were pipetted in tubes, coated with peptides P146-164 (SEQ ID NO. 6), P146-163 (SEQ ID NO. 7), P146-162 (SEQ ID NO. 8), P146-161 (SEQ ID NO. 9), P146-159 (SEQ ID NO. 11), P146-158 (SEQ ID NO. 12) and P146-157 (SEQ ID NO. 13). For calculation of non-specific binding (NSB) only 250 µl PBS with 0.5% bovine serum albumin (protease free) were pipetted in tubes, coated with peptides P146-164 (SEQ ID NO. 6), P146-163 (SEQ ID NO. 7), P146-162 (SEQ ID NO. 8), P146-161 (SEQ ID NO. 9), P146-159 (SEQ ID NO. 11), P146-158 (SEQ ID NO. 12) and P146-157 (SEQ ID NO. 13). The tubes were incubated over night at 22° C. under agitation. Then, the tubes were washed 5 times with 1 mL of B.R.A.H.M.S washing solution (B.R.A.H.M.S GmbH). In the second incubation step 200 µl of donkey-anti-sheep IgG tracer were added and the tubes were incubated for 2 hours at 22° C. under agitation. Then, the tubes were washed 5 times with 1 mL of B.R.A.H.M.S washing solution and bound chemiluminescence was measured for 1 s per tube with an LB 952T luminometer (Berthold).

d) mAb 429/F4 and mAb 423/F10

Tracer was produced by diluting the labeled antibody goat-anti-mouse IgG into assay buffer (PBS, 0.5% protease free bovine serum albumin) containing 106 relative light units (RLU) of MACN-labeled antibody per 200 µl. Monoclonal antibodies 429/F4 and 423/F10 were diluted with PBS, 0.5% bovine serum albumin (protease free) to the following concentrations: 972, 324, 108, 36 and 12 ng/200 µl.

In the first incubation step 50 µl of the dilutions of mAb 429/F4/mAb 423/F10 and 200 µl PBS, 0.5% bovine serum albumin (protease free) were pipetted in tubes, which were coated with peptides P146-164 (SEQ ID NO. 6), P146-163 (SEQ ID NO. 7), P146-162 (SEQ ID NO. 8), P146-161 (SEQ ID NO. 9), P146-159 (SEQ ID NO. 11), P146-158 (SEQ ID NO. 12) and P146-157 (SEQ ID NO. 13). For calculation of NSB, only 250 µl PBS, 0.5% bovine serum albumin (protease free) were pipetted in tubes, coated with peptides P146-164 (SEQ ID NO. 6), P146-163 (SEQ ID NO. 7), P146-162 (SEQ ID NO. 8), P146-161 (SEQ ID NO. 9), P146-159 (SEQ ID NO. 11), P146-158 (SEQ ID NO. 12) and P146-157 (SEQ ID NO. 13). The tubes were incubated over night at 22° C. under agitation. Then, the tubes were washed 5 times with 1 mL of B.R.A.H.M.S washing solution (B.R.A.H.M.S GmbH, Hennigsdorf, Germany). In the second incubation step 200 µl of goat-anti-mouse tracer were added and the tubes were incubated for 2 hours at 22° C. under agitation. Then, the tubes were washed 5 times with 1 mL of B.R.A.H.M.S washing solution and bound chemiluminescence was measured for 1 s per tube with an LB 952T luminometer (Berthold).

In FIGS. 1 (A) to 1 (D) the observed binding of the antiserum and antibodies to peptides representing C-terminally full-length and truncated variants of the C-terminal part of Copeptin (SEQ ID NO. 2) is shown. Anti-PLAY17 sheep antiserum, affinity purified sheep polyclonal anti-PLAY17 antibody and mAb 429/F4 exhibited comparable binding to peptides corresponding to amino acid positions 146-164 (SEQ ID NO. 6), 146-163 (SEQ ID NO. 7), 146-162 (SEQ ID NO. 8), 146-161 (SEQ ID NO. 9) of prepro-Vasopressin (SEQ ID NO. 1). With peptide variants, which were C-terminally more truncated, binding was reduced. The amount of reduction was dependent on the concentrations of the antibodies applied. For the antisera/antibodies tested it is concluded that their epitopes do not contain amino acid positions 161-164 of prepro-Vasopressin (SEQ ID NO. 1). In contrast, binding of mAb 423/F10 was only efficient against a peptide corresponding to amino acid positions 146-164 (SEQ ID NO. 6) of prepro-Vasopressin (SEQ ID NO. 1), and was strongly reduced against C-terminally truncated peptide variants. Thus, in the epitope of mAb 423/F10 amino acid position 164 of prepro-Vasopressin (SEQ ID NO. 1) is contained.

Immunoassays

Labeling of Monoclonal Antibodies

Labeling was done by standard procedures (EP 1488209 A1, EP 1738178 A1): The concentration of the purified antibodies 429/F4 and 423/F10 was adjusted to 1 g/L, and the antibodies were labeled by incubation with the chemiluminescent label MACN-Acridinium-NHS-Ester (1 g/L; InVent GmbH, Hennigsdorf, Germany) in a 1:5 molar ratio for 20 min at room temperature. The reactions were stopped by addition of 1/10 volume of 1 mol/L Tris for 10 min at room temperature. Labeled antibodies were separated from free label by size-exclusion chromatography on an NAP-5 column (GE Healthcare, Freiburg, Germany) and a Thermo BioBasic 300 5 µm HPLC column (Thermo Scientific).

Three sandwich immunoassays were utilized or developed as follows:

A. Pc Anti-PLAY17/Mc Anti-PATV17

CT-proAVP LIA (B.R.A.H.M.S GmbH, Hennigsdorf, Germany) as described in [7].

B. mAb 429/F4/Mc Anti-PATV17

Tracer was produced by diluting the labeled antibody 429/F4 into assay buffer (300 mmol/L potassium phosphate, 100 mmol/L NaCl, 10 mmol/L sodium EDTA, 5 g/L protease free bovine serum albumin, 1 g/L nonspecific sheep IgG, 1 g/L nonspecific bovine IgG, 1 g/L nonspecific mouse IgG, 0.9 g/L sodium azide, pH 7.0) containing 106 relative light units (RLU) of MACN-labeled antibody per 200 µl. 50 µl CT pro-AVP standards (B.R.A.H.M.S GmbH, Hennigsdorf, Germany)/samples and 200 µl of tracer were pipetted in CT pro-AVP coated tubes (B.R.A.H.M.S GmbH). The tubes were incubated for 2 hours at 22° C. under agitation. Then, the tubes were washed 5 times with 1 mL of washing solution (B.R.A.H.M.S GmbH), and bound chemiluminescence was measured for 1 s per tube with an LB 952T luminometer (Berthold).

C. mAb 423/F10/Mc Anti-PATV17

Tracer was produced by diluting the labeled antibodies 423/F10 into assay buffer (300 mmol/L potassium phosphate, 100 mmol/L NaCl, 10 mmol/L sodium EDTA, 5 g/L protease free bovine serum albumin, 1 g/L nonspecific sheep IgG, 1 g/L nonspecific bovine IgG, 1 g/L nonspecific mouse IgG, 0.9 g/L sodium azide, pH 7.0) containing 106 relative light units (RLU) of MACN-labeled antibody per 200 µl. 50 µl CT pro-AVP standards (B.R.A.H.M.S GmbH, Hennigsdorf, Germany)/samples and 200 µl of tracer were pipetted in CT pro-AVP coated tubes (B.R.A.H.M.S GmbH). The tubes were incubated for 2 hours at 22° C. under agitation. Then, the tubes were washed 5 times with 1 mL of washing solution (B.R.A.H.M.S GmbH), and bound chemiluminescence was measured for 1 s per tube with an LB 952T luminometer (Berthold).

Typical dose response curves for the three assays are shown in FIG. 2.

Method Comparison

With the three assays described above, various clinical samples were measured, including samples from healthy individuals, patients with cardiological diseases and patients from the ICU. Graphical method comparisons are shown in FIG. 3 (sera) and FIG. 4 (EDTA-plasma samples). Ideal Spearman correlation coefficients were observed, when assay pc anti-PLAY17/mc anti-PATV17 was compared with assay mAb 429/F4/mAb PATV17, whereas clear differences were observed, when assay mAb 423/F10/mc anti-PATV17 was compared to pc anti-PLAY17/mc anti-PATV17 or assay mAb 429/F4/mc anti-PATV17. The differences were more pronounced with sera than with EDTA-plasma samples. The differences observed are clearly associated with the epitopes of the antibodies: The epitope of mAb 423/F10 contains amino acid position 164 of prepro-Vasopressin (SEQ ID NO. 1), whereas the epitopes of pc anti-PLAY17 and mAb 429/F4 do not contain amino acid positions 161-164 of prepro-Vasopressin (SEQ ID NO. 1). Apparently, besides full-length Copeptin (SEQ ID NO. 2) there are also C-terminally truncated variants present in both, serum and plasma. As the samples used in the method comparison had been frozen immediately after harvesting and were thawed immediately prior to its measurement, the partial C-terminal truncation apparently had not occurred as a consequence of ex vivo storage, but had occurred already in vivo.

Analyte Stability

A subset of serum samples used in the method comparisons was stored for different periods at 22° C. and then measured with the three assays. By using the mAb 423/F10/mc anti-PATV17 assay, the recovery dropped drastically, already after 1 day storage at 22° C. The epitope of mAb 423/F10 contains amino acid position 164 of prepro-Vasopressin (SEQ ID NO. 1). In contrast, the analyte appeared much more stable when either the pc anti-PLAY17/mc anti-PATV17 or mAb 429/F4/mc anti-PATV17 assay was used. The epitopes of pc anti-PLAY17 and mAb 429/F4 do not contain amino acid positions 161-164 of prepro-Vasopressin (SEQ ID NO. 1).

```
                                Sequences

SEQ ID NO. 1 (prepro-Vasopressin)
         10         20         30         40         50         60
MPDTMLPACF LGLLAFSSAC YFQNCPRGGK RAMSDLELRQ CLPCGPGGKG RCFGPSICCA
         70         80         90        100        110        120
DELGCFVGTA EALRCQEENY LPSPCQSGQK ACGSGGRCAA FGVCCNDESC VTEPECREGF
        130        140        150        160
HRRARASDRS NATQLDGPAG ALLLRLVQLA GAPEPFEPAQ PDAY SEQ ID NO. 2 (Copeptin)
ASDRSNATQLDGPAGALLLRLVQLAGAPEPFEPAQPDAY
(representing amino acid positions 126-164 of prepro-Vasopressin (SEQ ID NO. 1))

SEQ ID NO. 3 (Peptide PAY14 )
CAPEPFEPAQPDAY
(representing amino acid positions 152-164 of prepro-Vasopressin (SEQ ID NO. 1) plus
an N-terminal cysteine)
```

| Sequences |
|---|

SEQ ID NO. 4 (Peptide PAY16)
CAGAPEPFEPAQPDAY
(representing amino acid positions 150-164 of prepro-Vasopressin (SEQ ID NO. 1) plus an N-terminal cysteine)

SEQ ID NO. 5 (Peptide PAY33)
ATQLDGPAGALLLRLVQLAGAPEPFEPAQPDAY
(representing amino acid positions 132-164 of prepro-Vasopressin (SEQ ID NO. 1))

SEQ ID NO. 6 (Peptide P146-164)
LVQLAGAPEPFEPAQPDAY
(representing amino acid positions 146-164 of prepro-Vasopressin (SEQ ID NO. 1))

SEQ ID NO. 7 (Peptide P146-163)
LVQLAGAPEPFEPAQPDA
(representing amino acid positions 146-163 of prepro-Vasopressin (SEQ ID NO. 1))

SEQ ID NO. 8 (Peptide P146-162)
LVQLAGAPEPFEPAQPD
(representing amino acid positions 146-162 of prepro-Vasopressin (SEQ ID NO. 1))

SEQ ID NO. 9 (Peptide P146-161)
LVQLAGAPEPFEPAQP
(representing amino acid positions 146-161 of prepro-Vasopressin (SEQ ID NO. 1))

SEQ ID NO. 10 (Peptide P146-160)
LVQLAGAPEPFEPAQ
(representing amino acid positions 146-160 of prepro-Vasopressin (SEQ ID NO. 1))

SEQ ID NO. 11 (Peptide P146-159)
LVQLAGAPEPFEPA
(representing amino acid positions 146-159 of prepro-Vasopressin (SEQ ID NO. 1))

SEQ ID NO. 12 (Peptide P146-158)
LVQLAGAPEPFEP
(representing amino acid positions 146-158 of prepro-Vasopressin (SEQ ID NO. 1))

SEQ ID NO. 13 (Peptide P146-157)
LVQLAGAPEPFE
(representing amino acid positions 146-157of prepro-Vasopressin (SEQ ID NO. 1))

SEQ ID NO. 14 (Anti-PATV17 Immunogen)
CATQLDGPAGALLLRLV
(representing positions 132-147 of pre-pro-Vasopressin (SEQ ID NO. 1) plus an N-terminal cystein residue)

SEQ ID NO. 15 (Anti-PLAY17 Immunogen)
CLAGAPEPFEPAQPDAY
(representing positions 149-164 of pre-pro-Vasopressin (SEQ ID NO. 1) plus an N-terminal cystein residue)

SEQ ID NO. 16 (294/1A7 Immunogen)
ATQLDGPAGALLLRLVQLAGAPEPFEPAQPDAY
(representing positions 132-164 of pre-pro-Vasopressin (SEQ ID NO. 1) plus an N-terminal cystein residue)

SEQ ID NO. 17 (H-065-32 Immunogen)
ASDRSNATQLDGPAGALLLRLVQLAGAPEPFEPAQPDAY
(representing positions 126-164 of prepro-Vasopressin (SEQ ID NO. 1))

SEQ ID NO. 18 (MAB6077 (clone 579021) Immunogen)
ASDRSNATQLDGPAG
(representing positions 126-140 of pre-pro-Vasopressin (SEQ ID NO. 1))

SEQ ID NO. 19 (MAG-1 Immunogen)
QLAGAPEPFEPAQPDAY
(representing positions 148-164 of pre-pro-Vasopressin (SEQ ID NO. 1))

SEQ ID NO. 20 (294/1A7 Epitope)
GPAGAL
(representing positions 137-144 of pre-pro-Vasopressin (SEQ ID NO. 1))

SEQ ID NO. 21
GALLLRLVQLAGAPEPFEPAQPDA
(representing positions 140-163 of pre-pro-Vasopressin (SEQ ID NO. 1))

```
                              Sequences

SEQ ID NO. 22
LLLRLVQLAGAPEPFEPAQPDA
(representing positions 142-163 of pre-pro-Vasopressin (SEQ ID NO. 1))

SEQ ID NO. 23
LRLVQLAGAPEPFEPAQPDA
(representing positions 144-163 of pre-pro-Vasopressin (SEQ ID NO. 1))
```

LITERATURE

1. Kluge M, Riedl S, Erhart-Hofmann B, Hartmann J, Waldhauser F. Improved extraction procedure and RIA for determination of arginine-8-vasopressin in plasma: role of premeas-urement sample treatment and reference values in children. Clin Chem 1999; 45:98-103.
2. Preibisz J J, Sealey J E, Laragh J H, Cody R J, Weksler B B. Plasma and platelet vasopressin in essential hypertension and congestive heart failure. Hypertension 1983; 5:1129-38.
3. Robertson G L, Mahr E A, Athar S, Sinha T. Development and clinical application of a new method for the radio-immunoassay of arginine vasopressin in human plasma. J Clin Invest 1973; 52:2340-52.
4. Morgenthaler N G, Struck J, Alonso C, Bergmann A. Assay for the measurement of co-peptin, a stable peptide derived from the precursor of vasopressin. Clin Chem 2006; 52:112-9.
5. Morgenthaler N G, Struck J, Jochberger S, Dunser M W. Copeptin: clinical use of a new biomarker. Trends Endocrinol Metab 2008; 19:43-9.
6. Struck J, Morgenthaler N G, Bergmann A. Copeptin, a stable peptide derived from the vasopressin precursor, is elevated in serum of sepsis patients. Peptides 2005; 26:2500-4.
7. Fenske W, Stork S, Blechschmidt A, Maier S G, Morgenthaler N G, Allolio B. Copeptin in the differential diagnosis of hyponatremia. J Clin Endocrinol Metab 2009; 94:123-9.

What is claimed is:

1. A monoclonal antibody capable of binding to an epitope contained in an amino acid sequence of the C-terminal part of prepro-vasopressin (SEQ ID NO. 1) comprising amino acids 146-163, but lacking amino acid 164, the monoclonal antibody being 429/F4.

2. A hybridoma cell line producing a monoclonal antibody capable of binding to an epitope contained in an amino acid sequence of the C-terminal part of prepro-vasopressin (SEQ ID NO. 1) comprising amino acids 146-163, but lacking amino acid 164, the hybridoma cell line producing monoclonal antibody 429/F4.

* * * * *

```
                              SEQUENCE LISTING

<160> NUMBER OF SEQ ID NOS: 23

<210> SEQ ID NO 1
<211> LENGTH: 164
<212> TYPE: PRT
<213> ORGANISM: Homo sapiens

<400> SEQUENCE: 1

Met Pro Asp Thr Met Leu Pro Ala Cys Phe Leu Gly Leu Leu Ala Phe
1               5                   10                  15

Ser Ser Ala Cys Tyr Phe Gln Asn Cys Pro Arg Gly Gly Lys Arg Ala
            20                  25                  30

Met Ser Asp Leu Glu Leu Arg Gln Cys Leu Pro Cys Gly Pro Gly Gly
        35                  40                  45

Lys Gly Arg Cys Phe Gly Pro Ser Ile Cys Cys Ala Asp Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Ala Phe Gly Val Cys Cys Asn Asp Glu Ser Cys Val Thr
            100                 105                 110

Glu Pro Glu Cys Arg Glu Gly Phe His Arg Arg Ala Arg Ala Ser Asp
        115                 120                 125

Arg Ser Asn Ala Thr Gln Leu Asp Gly Pro Ala Gly Ala Leu Leu Leu
    130                 135                 140

Arg Leu Val Gln Leu Ala Gly Ala Pro Glu Pro Phe Glu Pro Ala Gln
145                 150                 155                 160

Pro Asp Ala Tyr

<210> SEQ ID NO 2
<211> LENGTH: 39
```

```
<212> TYPE: PRT
<213> ORGANISM: Homo sapiens

<400> SEQUENCE: 2

Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
                20                  25                  30

Pro Ala Gln Pro Asp Ala Tyr
            35

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

Cys Ala Pro Glu Pro Phe Glu Pro Ala Gln Pro Asp Ala Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Cys Ala Gly Ala Pro Glu Pro Phe Glu Pro Ala Gln Pro Asp Ala Tyr
1               5                   10                  15

<210> SEQ ID NO 5
<211> LENGTH: 33
<212> TYPE: PRT
<213> ORGANISM: Artificial Sequence
<220> FEATURE:
<223> OTHER INFORMATION: Synthetic

<400> SEQUENCE: 5

Ala Thr Gln Leu Asp Gly Pro Ala Gly Ala Leu Leu Leu Arg Leu Val
1               5                   10                  15

Gln Leu Ala Gly Ala Pro Glu Pro Phe Glu Pro Ala Gln Pro Asp Ala
                20                  25                  30

Tyr

<210> SEQ ID NO 6
<211> LENGTH: 19
<212> TYPE: PRT
<213> ORGANISM: Artificial Sequence
<220> FEATURE:
<223> OTHER INFORMATION: Synthetic

<400> SEQUENCE: 6

Leu Val Gln Leu Ala Gly Ala Pro Glu Pro Phe Glu Pro Ala Gln Pro
1               5                   10                  15

Asp Ala Tyr

<210> SEQ ID NO 7
<211> LENGTH: 18
<212> TYPE: PRT
<213> ORGANISM: Artificial Sequence
<220> FEATURE:
```

<223> OTHER INFORMATION: Synthetic

<400> SEQUENCE: 7

Leu Val Gln Leu Ala Gly Ala Pro Glu Pro Phe Glu Pro Ala Gln Pro
1               5                   10                  15

Asp Ala

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Leu Val Gln Leu Ala Gly Ala Pro Glu Pro Phe Glu Pro Ala Gln Pro
1               5                   10                  15

Asp

<210> SEQ ID NO 9
<211> LENGTH: 16
<212> TYPE: PRT
<213> ORGANISM: Artificial Sequence
<220> FEATURE:
<223> OTHER INFORMATION: Synthetic

<400> SEQUENCE: 9

Leu Val Gln Leu Ala Gly Ala Pro Glu Pro Phe Glu Pro Ala Gln Pro
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Leu Val Gln Leu Ala Gly Ala Pro Glu Pro Phe Glu Pro Ala Gln
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: Synthetic

<400> SEQUENCE: 11

Leu Val Gln Leu Ala Gly Ala Pro Glu Pro Phe Glu Pro Ala
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Leu Val Gln Leu Ala Gly Ala Pro Glu Pro Phe Glu Pro
1               5                   10

<210> SEQ ID NO 13
<211> LENGTH: 12

```
<212> TYPE: PRT
<213> ORGANISM: Artificial Sequence
<220> FEATURE:
<223> OTHER INFORMATION: Synthetic

<400> SEQUENCE: 13

Leu Val Gln Leu Ala Gly Ala Pro Glu Pro Phe Glu
1               5                   10

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Cys Ala Thr Gln Leu Asp Gly Pro Ala Gly Ala Leu Leu Leu Arg Leu
1               5                   10                  15

Val

<210> SEQ ID NO 15
<211> LENGTH: 17
<212> TYPE: PRT
<213> ORGANISM: Artificial Sequence
<220> FEATURE:
<223> OTHER INFORMATION: Synthetic

<400> SEQUENCE: 15

Cys Leu Ala Gly Ala Pro Glu Pro Phe Glu Pro Ala Gln Pro Asp Ala
1               5                   10                  15

Tyr

<210> SEQ ID NO 16
<211> LENGTH: 33
<212> TYPE: PRT
<213> ORGANISM: Artificial Sequence
<220> FEATURE:
<223> OTHER INFORMATION: Synthetic

<400> SEQUENCE: 16

Ala Thr Gln Leu Asp Gly Pro Ala Gly Ala Leu Leu Leu Arg Leu Val
1               5                   10                  15

Gln Leu Ala Gly Ala Pro Glu Pro Phe Glu Pro Ala Gln Pro Asp Ala
                20                  25                  30

Tyr

<210> SEQ ID NO 17
<211> LENGTH: 39
<212> TYPE: PRT
<213> ORGANISM: Artificial Sequence
<220> FEATURE:
<223> OTHER INFORMATION: Synthetic

<400> SEQUENCE: 17

Ala Ser Asp Arg Ser Asn Ala Thr Gln Leu Asp Gly Pro Ala Gly Ala
1               5                   10                  15

Leu Leu Leu Arg Leu Val Gln Leu Ala Gly Ala Pro Glu Pro Phe Glu
                20                  25                  30

Pro Ala Gln Pro Asp Ala Tyr
        35

<210> SEQ ID NO 18
```

```
<211> LENGTH: 15
<212> TYPE: PRT
<213> ORGANISM: Artificial Sequence
<220> FEATURE:
<223> OTHER INFORMATION: Synthetic

<400> SEQUENCE: 18

Ala Ser Asp Arg Ser Asn Ala Thr Gln Leu Asp Gly Pro Ala Gly
1               5                   10                  15

<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Gln Leu Ala Gly Ala Pro Glu Pro Phe Glu Pro Ala Gln Pro Asp Ala
1               5                   10                  15

Tyr

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Gly Pro Ala Gly Ala Leu
1               5

<210> SEQ ID NO 21
<211> LENGTH: 24
<212> TYPE: PRT
<213> ORGANISM: Artificial Sequence
<220> FEATURE:
<223> OTHER INFORMATION: Synthetic

<400> SEQUENCE: 21

Gly Ala Leu Leu Leu Arg Leu Val Gln Leu Ala Gly Ala Pro Glu Pro
1               5                   10                  15

Phe Glu Pro Ala Gln Pro Asp Ala
            20

<210> SEQ ID NO 22
<211> LENGTH: 22
<212> TYPE: PRT
<213> ORGANISM: Artificial Sequence
<220> FEATURE:
<223> OTHER INFORMATION: Synthetic

<400> SEQUENCE: 22

Leu Leu Leu Arg Leu Val Gln Leu Ala Gly Ala Pro Glu Pro Phe Glu
1               5                   10                  15

Pro Ala Gln Pro Asp Ala
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic
```

```
<400> SEQUENCE: 23

Leu Arg Leu Val Gln Leu Ala Gly Ala Pro Glu Pro Phe Glu Pro Ala
1               5                   10                  15

Gln Pro Asp Ala
            20
```